United States Patent [19]

Wardlaw

[11] Patent Number: 4,683,579
[45] Date of Patent: * Jul. 28, 1987

[54] METHOD AND APPARATUS FOR MEASURING BLOOD CONSTITUENT COUNTS

[76] Inventor: Stephen C. Wardlaw, 128 Sunset Hill Dr., Branford, Conn. 06405

[*] Notice: The portion of the term of this patent subsequent to Dec. 17, 2002 has been disclaimed.

[21] Appl. No.: 813,978

[22] Filed: Dec. 27, 1985

[51] Int. Cl.⁴ .................. G01N 15/02; G01N 21/00
[52] U.S. Cl. .................................. 377/11; 356/39; 356/338; 250/338
[58] Field of Search .................. 356/36, 39, 338; 250/339, 338, 341; 377/10, 11

[56] References Cited

U.S. PATENT DOCUMENTS

| | | | |
|---|---|---|---|
| 3,349,227 | 10/1967 | Martens et al. | 377/11 |
| 4,027,971 | 6/1977 | Kolman et al. | 356/39 |
| 4,528,680 | 7/1985 | Archambeault | 377/10 |
| 4,558,947 | 12/1985 | Wardlaw | 356/39 |

Primary Examiner—John S. Heyman
Attorney, Agent, or Firm—William W. Jones

[57] ABSTRACT

Blood constituents such as red cells, white cells, and platelets are centrifuged into layers in a capillary tube and the true extent of one or more of the layers is measured photometrically. Each layer to be measured is optically scanned by a sequence of scanning operations with the actual extent of each layer traverse being recorded in a computer. After each layer has been completely circumferentially scanned and each traverse recorded, the computer determines the true average axial dimension for each layer and computes, through prior input, the actual constituent count for each constituent layer.

9 Claims, 9 Drawing Figures

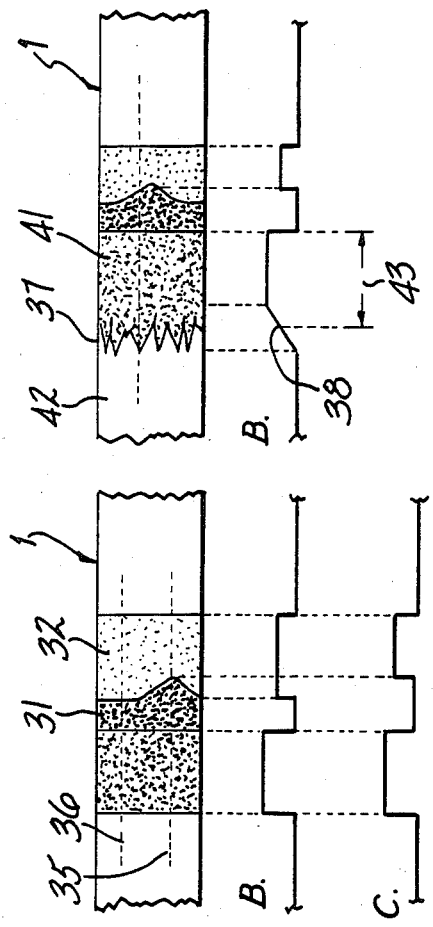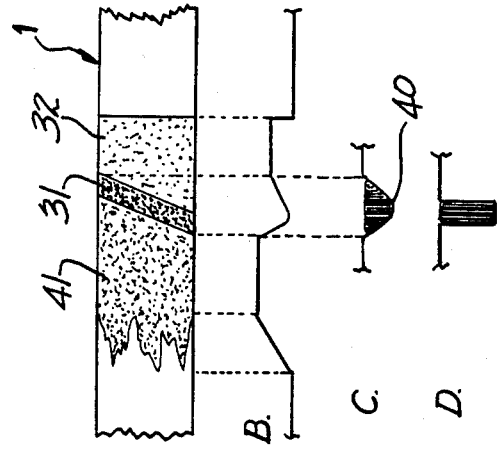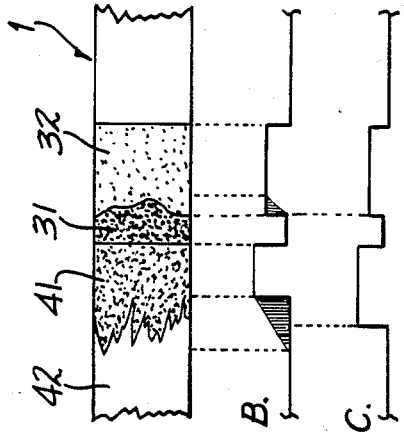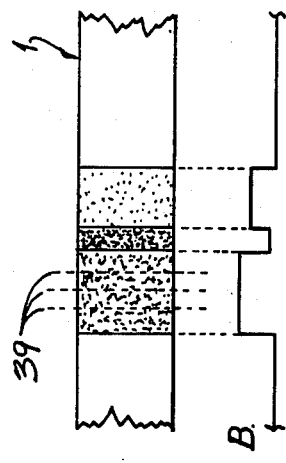

METHOD AND APPARATUS FOR MEASURING BLOOD CONSTITUENT COUNTS

This invention relates to an improved method and apparatus for measuring substantially accurate blood constituent counts in a centrifuged sample of anticoagulated whole blood.

U.S. Pat. Nos. 4,027,660; 4,082,085; and 4,137,755 relate to apparatus and methodology for physically elongating blood constituent layers in a centrifuged capillary tube blood sample. U.S. Pat. No. 4,156,570 relates to an instrument for obtaining blood constituent counts from the physically elongated constituent layers derived as in the first referenced patents.

These previous patents have shown how the constituent layers in a sample of centrifuged blood may be measured by adding a fluorescent stain, such as acridine orange, and illuminating the cell layers with a light at a first wavelength. This will cause the fluorescent stain to emit light at another wavelength, where a scanning device measures the light at this second wavelength and uses the information to determine the boundaries of said cell layers. Once the boundaries are determined, the areas of the constituent cell layers can be calculated, and these can be converted into clinically meaningful units.

One problem with this type of device is that all fluorescent measurements require considerable quantities of power and require high quality optical systems and filters. These factors tend to make an instrument expensive, less reliable and difficult to adapt for use with batteries.

It is the object of this invention to produce a reader which has the same capability of cell layer separation as the fluorescent reader, but which does not have the same stringent design requirements.

I have found that light, particularly light in the near infra-red region, can be scattered from the constituent cell layers, and that this scattering is different for each layer component, enabling differentiation of the layers. If a light source is placed so that the beam of illumination strikes the tube at a narrow angle relative to the axis of the tube, the packed cell layers will scatter the light at roughly right angles, but the beam striking the tube directly will be reflected at the same, narrow incident angle. The incident angle of the illuminating light can be any which allows the reflected beam to miss the detector, which is at right angles to the tube axis. The preferred angle is about 20°. A detector, preferably placed at right angles to the tube, can detect the scattered light and provide a "map" of the layer boundaries by virtue of their differing light scattering properties. The light wavelengths used can vary from 400–1000 mu, but the preferred wavelengths are near 800 mu. A normal, unfiltered, incandescent lamp can supply intense light at these wavelengths as can an infra-red light emitting diode (LED).

The preferred mode of operation is to use an LED as the source of illumination and a solid state photodetector as the sensing element of the scanner. Most preferably, the LED will be used in a pulse mode, where it is turned on repetitively, but only for a brief period of time. The signal from the detector is sampled by an analog-digital converter, but only at the time that the LED is on. This effectively eliminates the effect of stray room light and allows the reader instrument to be used without any elaborate shielding.

The advantages of this invention will be more readily apparent from the following detailed description of preferred embodiments of the method and apparatus thereof when taken in conjunction with the accompanying drawings, in which:

FIG. 4 is a schematic plan view of a first cell layer interface which may be achieved by centrifugation;

FIG. 5 is a schematic plan view of a second cell layer interface which may be achieved by centrifugation;

FIG. 6 is a schematic plan view of a third cell layer interface which may be achieved by centrifugation:

FIG. 7 is a schematic plan view of a cell layer interface similar to that shown in FIG. 4;

FIG. 8 is a schematic plan view of a cell layer interface similar to that shown in FIG. 6; and FIG. 9 is a schematic plan view of a fourth cell layer interface which may be achieved by centrifugation.

Figure 1:
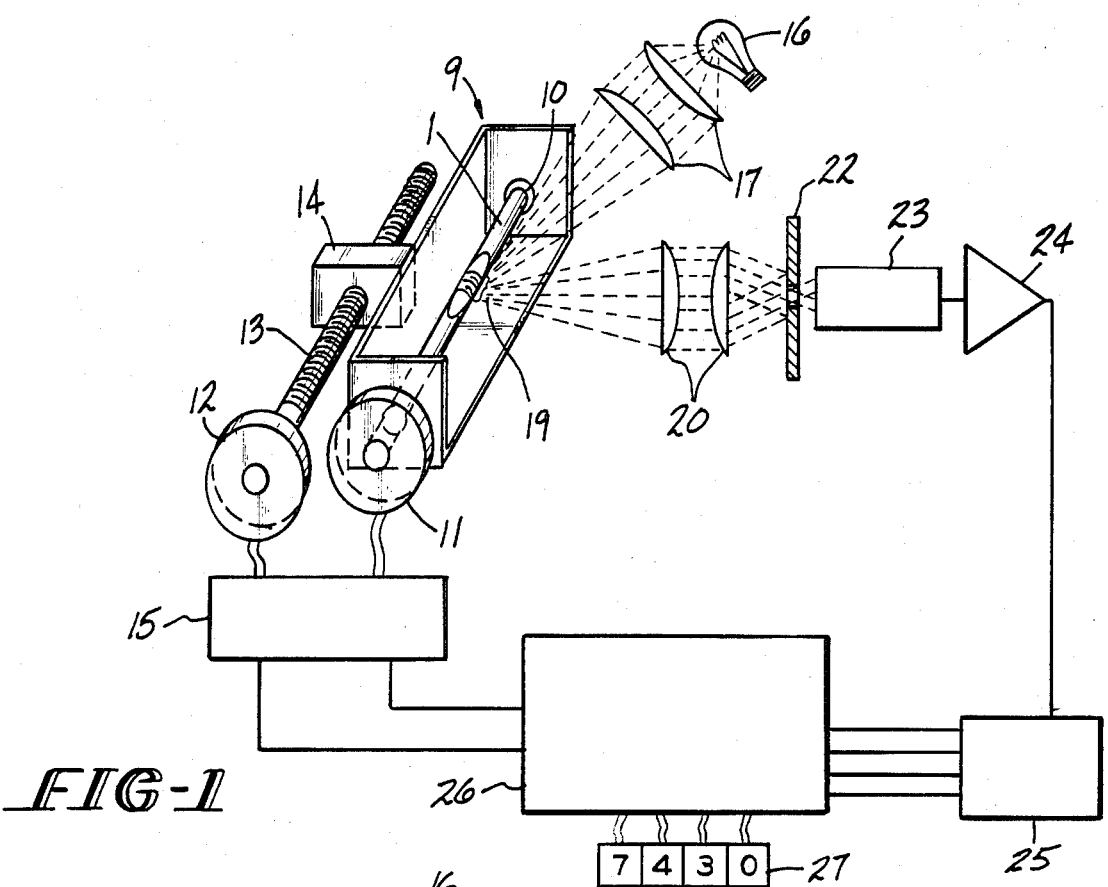
FIG. 1 is a somewhat schematic perspective view of a preferred embodiment of an apparatus for performing cell count measurements in accordance with this invention.

Referring now to the drawings, there is shown in FIG. 1 a schematic perspective view of one preferred embodiment of an apparatus formed in accordance with this invention. It will be understood that the blood sample-containing tube 1 shown in the drawing contains a centrifuged anticoagulated whole blood sample and a float body as described in the aforesaid U.S. Pat. No. 4,082,085. The tube 1 is supported at each end by self-centering spring loaded mandrels 10 which are incrementally rotated by a stepping motor 11. The motor 11 preferably rotates the mandrels 10 and tube 1 through successive angles of about 6° or 360° as will be explained hereinafter. The mandrels 10 and motor 11 are mounted on a frame 9 which, in turn, is secured to an internally threaded bushing block 14. The block 14 receives a threaded rod 13, which is rotated by a reversible stepping motor 12. The motor 12 and the rod 13 are mounted on a fixed frame (not shown) and the block 14 is keyed to the fixed frame so that the block 14, frame 9, motor 11, mandrels 10 and tube 1 will undergo reciprocal linear movement in the direction of the axis of the tube 1 as the rod 13 is rotated by the motor 12. Thus, as the motor 12 operates through a forward and reverse cycle, the rod 1 will move in one direction along its axis and return in the opposite direction. The extent of movement is such that the buffy coat-containing area 19 of the tube 1 can be scanned by the apparatus in the manner detailed hereinafter. The stepping motors 11 and 12 are driven by a stepping motor driver 15.

A light source, such as an incandescent lamp 16 or a light-emitting diode (LED), is mounted on the fixed frame so as to direct light toward the area 19 of the tube 1. Lenses 17 are operable to focus light emitted by the lamp 16 on the area 19 of the tube. If an LED is used, the lenses 17 are integrally moulded as part of the LED.

The emitted light is collected by lenses 20 and impinges upon photodiode 23. A diaphragm 22 is positioned in front of the photodiode 23 so as to restrict the field of light passing to the phototube 23 to a spot which, in this instance, is preferably about 100 microns in diameter. An amplifier 24 is connected to the photodiode 23 and is operable to amplify the photoelectric signals generated by the photodiode 24 and transmit the amplified signals to a converter 25, which converts the signals from analog to digital form. The converter 25 is connected to a computer 26. The computer 26 controls the converter 25 and also controls the stepping motors 11 and 12. The computer 26 can operate the device in one of two ways. The computer 26 can direct the converter 25 to take a reading and at the same time direct the stepping motor 11 to rotate the tube 1 stepwise through a 360° angle. The readings are then stored in the computer 26. The computer then directs the stepping motor 12 to rotate the rod 13 through a known angle which will move the tube 1 a distance of 100 microns (the size of the window in the diaphragm 22). After the tube 1 is thus axially shifted, the computer 26 directs the converter 25 to take another set of readings and while directing the stepping motor 11 to once again rotate the tube 1 stepwise through another 360° angle. The second readings are then stored in the computer 26 and the procedure repeated a third time. The procedure is repeated until the entire target area 19 of the sample has been scanned and read. An alternative mode of operation involves the computer 26 directing the converter 25 to take a reading and then directing the stepping motor 12 to incrementally rotate the rod 13 sufficiently to shift the tube 1 axially so as to cause the entire axial extent of the target area 19 to be scanned. The readings are stored in the computer 26, and the computer 26 then directs the stepping motor 11 to rotate the tube 1 through a substantially 6° angle. The converter 25 is then directed to take another set of readings while the stepping motor 12 is directed to incrementally rotate the rod 13 in the opposite direction so as to shift the tube 1 back through the entire extent of the target area 19. This second procedure can then be repeated until the entire circumference of the target area 19 has been read and stored. In either of the above modes, the intensity of scatter of the entire target area 19 of the sample is mapped in the computer memory. The extent or area of each of the cell bands is then calculated by the computer 26 and converted into cell counts by use of cell size information, and radial band thickness information (the latter of which is equal to the radial thickness of the void or free space between the float body and the tube bore), which information has been previously inputted into the computer 26. The actual cell counts are then sequentially displayed in the digital readout frames 27.

Figure 3:
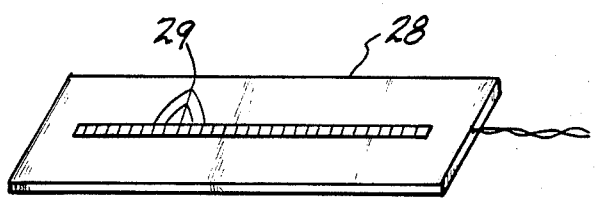
FIG. 3 is a perspective view of a component of the apparatus of FIG. 2.
Figure 2:
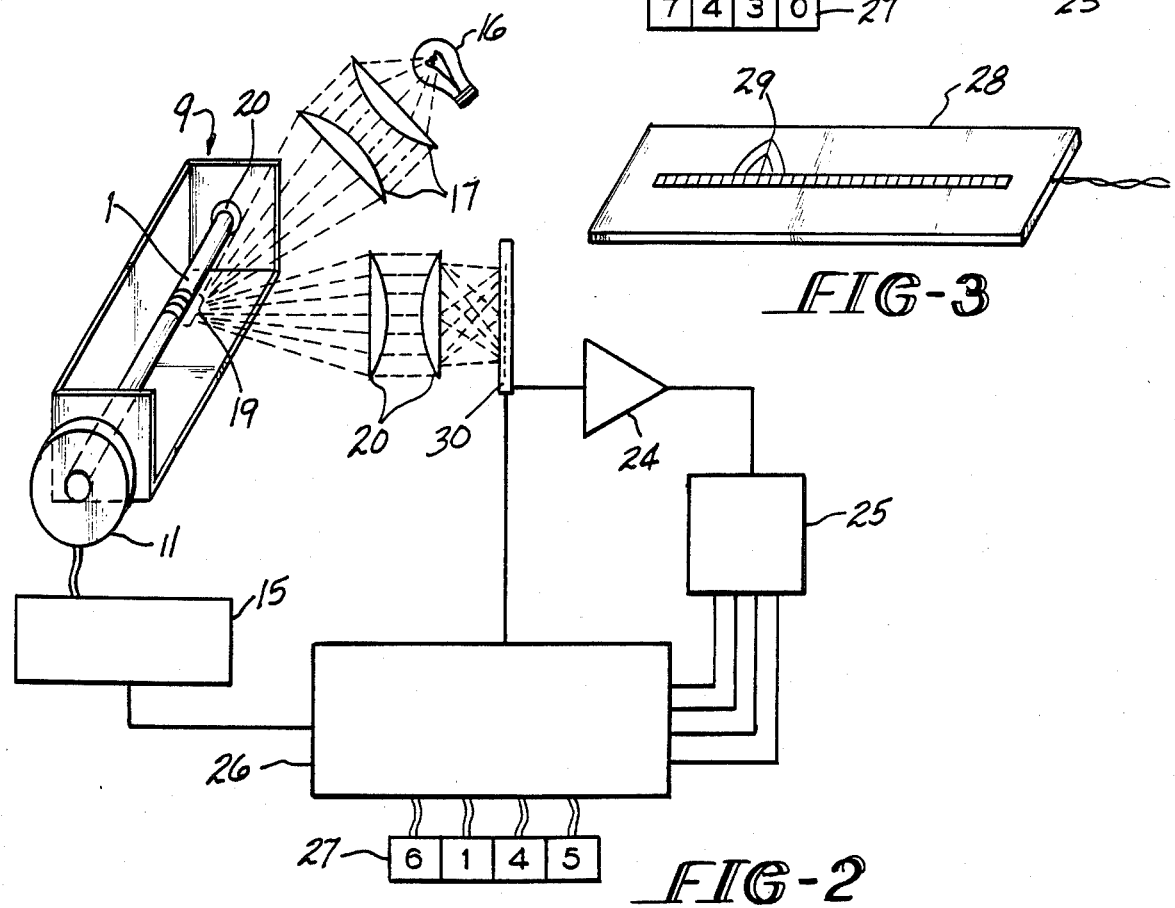
FIG. 2 is a somewhat schematic perspective view of a second embodiment of an apparatus for performing cell count measurements in accordance with this invention.

Referring now to FIG. 2, there is shown an alternative form of a reader apparatus which may be used. In the apparatus of FIG. 2, certain components are the same as in FIG. 1, and like numerals are used to designate such components. The apparatus of FIG. 2 includes mandrels 10 for holding the ends of the tube 1, which mandrels 10 are mounted in a frame 9 and rotated by a stepping motor 11 controlled by stepping motor driver 15. A lamp 16 is focused on target area 19 of the sample in the tube 1 by lenses 17, and the light is emitted by the lamp or LED 16, as previously described. Light scattered from the sample is focused by lenses 20 onto a linear array of photocells denoted generally by the numeral 30. The array 30, as seen in FIG. 3, includes a flat insulating substrate 28 on which there is placed a linear array of photocells 29. There can be as many as 1,024 photocells in a single commercially available array of the type shown in FIG. 3. The photosensing elements may be either of the diode (Reticon) or charge-coupled (Fairchild) type. When the image of the target area 19 is focused by the lenses 20 onto the photocells 29 in the array 30, scattered light intensity readings from each single cell 29 in the array 30 can be amplified by the amplifier 24 and converted into a digital signal by the converter 25 and fed into the computer 26, as previously described. Since the intensity of light scattering of a linear segment of the entire target area 19 is measured at once, the need to move the tube 1 axially is eliminated, and the tube 1 need only be rotated about its axis to bring the next circumferential region into view. Thus, the embodiment of FIG. 2 is less complex mechanically than the embodiment of FIG. 1. On the other hand, the arrays used in the embodiment of FIG. 2 may be somewhat less sensitive to light than the photodiode used in the embodiment of FIG. 1 and, thus, may not be as accurate in some instances.

Referring to FIGS. 4-9, there are shown various cell interfaces which may be formed by centrifugation of the blood sample along with schematic representations of the "map" of the cell layers which the computer has inputted into it from the converter. In FIG. 4, it will be noted that the granulocyte band 41, the lymphocyte/monocyte band 31 and the platelet band 32 have clear, sharp interfaces in the centrifuged sample. Examination of pixels along line 33 by the computer will produce a histogram B shown in FIG. 4. The horizontal axis of the histogram represents distances along the longitudinal axis of the blood sample, and the vertical axes in the histogram represent the various light scattering intensities of the various cells. With a sample as shown in FIG. 4, the computer need only search for obvious discontinuities in light scatter and measure the distances 34 between such discontinuities. Once the distances 34 are measured by the computer, they are multiplied by the known calibration factors to derive the various cell counts.

FIG. 5 shows a sample wherein the interface between the layers 31 and 32 is distorted by a bulge. The two histograms B and C in FIG. 5 show that single readings taken along lines 35 and 36 would indicate different axial dimensions for the cell layer 31 if such measurements were only made along lines 35 and 36. The computer obviates this problem, however, by averaging all of the separate measurements taken as the successive longitudinal scans are performed.

FIG. 6 shows a similar problem which arises with a jagged interface 37 between the cell layers 42 and 41. The histogram B for the sample in FIG. 6 will have a sloping interface 38 whereby the geometric mean of that sloping line 38 will provide the correct line to begin measurement of the axial dimension 43 of the cell layer 41. This geometric mean is calculated, as before, by the computer by analyzing each successive scan.

FIG. 7 shows a well delineated sample similar to FIG. 4 and shows the histogram B which is produced by circumferential sequential scans taken along lines 39. As with FIG. 4, the histogram will have well defined abrupt discontinuities which will be noted by the computer with no averaging being necessary.

FIG. 8 shows a sample which is similar to that shown in FIG. 6 in that the interface between the layers 41 and 42 is indistinct and the interface between the layers 31 and 32 is irregular. The histogram B of the sample in FIG. 8 shows the average circumferential readings, i.e., the readings taken in the direction of lines 39 shown in FIG. 7. The shaded areas of the histogram B represent the areas which must be interpolated to derive the corrected layer extents. This is performed by the computer by calculating the area of each shaded portion and converting it to a band length increment, assuming the same color intensity as the full intensity readings, which are delineated by the horizontal lines on the histogram B in FIG. 8. The corrected histogram is shown at C in FIG. 8.

FIG. 9 shows a layer formation in the cell layer 31 which can present a complicated problem when the scans are taken in the circumferential direction, as along the lines 39 shown in FIG. 7. In this type of layering, each linear scan can include some of the surrounding layers 41 or 32. This condition results in a histogram as shown at B in FIG. 9. In the area marked 40 in the histogram, there is no definable plateau of intensity, thus any interpretation of the width of the area 40 at this point would be erroneous. When such a condition is noted by the computer, it is programmed to perform a Fourier transformation of the irregular curve 40 with the result being shown at C in FIG. 9. The shaded area under the curve C of FIG. 9 represents the area of the layer 31. If the minimum intensity of the layer 31 is known, then the computer can calculate the true axial dimension of the layer 3 as shown at D in FIG. 9. To obtain the minimum intensity, it is only necessary to stop rotation of the tube and take one longitudinal or axial scan, locating and measuring the trough intensity of the layer in question.

The instrument can be programmed to read the absolute light scattering properties for each individual layer, as well as reading the differential light scattering properties of the several different layers. When absolute scattering is measured, the instrument can determine how tightly packed each cell layer is and can thus be programmed to compensate for noted differences in packing for similar cell layers in different samples. For example, if the instrument, by measuring absolute light scattering, determines that the monocyte band has its cells packed more tightly in one sample than in another, it will know that the more tightly packed band will have more cells in it than would otherwise be suspected.

These techniques could also be applied to the analysis of other regions of the blood sample. The reticulocytes (newly formed red blood cells) lie in a diffuse band adjacent to the granulocytes. The effective axial dimension of the reticulocyte layer can be calculated in a similar manner. If the diaphragm window were made small enough, about 20 microns in diameter, physical expansion of the buffy coat would not be required.

Since many changes and variations of the disclosed embodiments of the invention may be made without departing from the inventive concept, it is not intended to limit the invention otherwise than as required by the appended claims.

What is claime.d is:

1. An optical scanning apparatus for measuring blood cell counts in a centrifuged sample of anticoagulated whole blood contained in a transparent tube wherein the blood cell types are separated into different layers in the tube, said apparatus comprising:
    (a) means for supporting the tube;
    (b) a source of near infra-red region-light operable to illuminate the blood cell layers in the tube;
    (c) photosensor means focused on the illuminated blood cell layers in the tube and operable to scan the cell layers to detect differing light scattering properties of the different cell types in the layers of cells;
    (d) means for causing relative movement between the tube and said photosensor means for enabling said photosensor means to scan the layers of blood cells at all different locations circumferentially of the tube;
    (e) converter means operably connected to said photosensor means for converting analog signals from said photosensor means to digital form; and
    (f) computer means operably connected to said converter means for receiving and storing digital signals from said converter means, said computer means further being operable to utilize the signals received to calculate the average axial dimension of each layer of cells scanned to determine from previously inputted data the true cell counts for each layer of cells scanned.

2. The apparatus of claim 1 wherein said source of light is operable to cause a beam of illumination to strike said tube at an angle of about 20° to the axis of said tube.

3. The apparatus of claim 1 wherein said source of light is an infra-red emitting diode.

4. The apparatus of claim 3 wherein said diode is operated in a pulsating mode.

5. The apparatus of claim 1 wherein said photosensor means is a solid state photodetector.

6. The apparatus of claim 1 wherein said source of light emits light of wavelengths in the range of about 400 to about 1,000 mu.

7. A method for measuring blood cell counts in a centrifuged sample of anticoagulated whole blood contained in a transparent tube wherein the blood cell types are separated into different layers in the tube, said method comprising the steps of:
    (a) illuminating the cell layers to be measured with a substantially infra-red light source which produces differing light scattering properties in the different cell types being measured;
    (b) scanning the entire outer circumferential surface of each cell layer being measured with a photosensor which detects differing light scattering properties produced by illumination of the different cell types being measured and which photosensor produces an analog output which varies in proportion to the different scattering properties of light detected in the cell layers;
    (c) converting said analog output to digital output;
    (d) receiving and storing said digital output in a computer and thereafter computer analyzing said stored digital output to compute an average axial dimension for each layer of cells scanned and determining in said computer the true cell counts for each layer of cells scanned from the computed average axial dimension and additional previously inputted data stored in said computer.

8. The method of claim 7 wherein said illuminating step is performed intermittently in pulsating fashion.

9. The method of claim 7 wherein light beams impinge said cell layers in said tube at an angle of incidence of about 20° to the axis of said tube.

* * * * *